United States Patent
Lee et al.

(10) Patent No.: US 7,985,370 B2
(45) Date of Patent: Jul. 26, 2011

(54) APPARATUS FOR FORMING LONGITUDINAL THERMAL-FATIGUE CRACKS

(75) Inventors: Bo Young Lee, Goyang (KR); Jae Seong Kim, Goyang (KR); Woong Ki Hwang, Seoul (KR)

(73) Assignee: Industry-University Cooperation Foundation Hankuk Aviation University, Gyeonggi-do (KR)

( * ) Notice: Subject to any disclaimer, the term of this patent is extended or adjusted under 35 U.S.C. 154(b) by 408 days.

(21) Appl. No.: 12/325,726

(22) Filed: Dec. 1, 2008

(65) Prior Publication Data

US 2010/0109211 A1 May 6, 2010

(30) Foreign Application Priority Data

Oct. 31, 2008 (KR) ................ 10-2008-0107558

(51) Int. Cl.
*G01N 3/32* (2006.01)
(52) U.S. Cl. ............ 266/260; 266/259; 266/44; 73/808
(58) Field of Classification Search ............. 266/44, 266/46, 99, 259, 260; 148/508, 570, 574, 148/590; 73/808
See application file for complete search history.

(56) References Cited

U.S. PATENT DOCUMENTS

| 6,723,185 B1 * | 4/2004 | Elfving et al. ............ 148/508 |
| 7,559,251 B2 * | 7/2009 | Lee et al. .................. 73/808 |
| 2006/0113010 A1 * | 6/2006 | Saitou et al. ............. 148/570 |

FOREIGN PATENT DOCUMENTS

KR   1020070122349   12/2007

* cited by examiner

*Primary Examiner* — Scott Kastler
(74) *Attorney, Agent, or Firm* — IPLA P.A.; James E. Bame

(57) ABSTRACT

An apparatus for forming longitudinal thermal fatigue cracks. A heating unit has an induction coil disposed adjacent to an outer circumference of one side of a tubular test piece, on an inner surface of which a notch is formed. A cooling unit has a cooling water pump and a cooling water hose which forcibly injects cooling water from a cooling water storage source into an inner circumference of the tubular test piece. A control unit controls operation of the heating and cooling units. A cooling block partially encloses the outer circumference of the tubular test piece so as to control a magnitude of y-axial stress, is supplied with a cooling source of fluid or gas from an outside so as to repetitively cool the tubular test piece heated by the heating unit to adjust a temperature gradient, and has a longitudinal slit for controlling crack positions.

3 Claims, 7 Drawing Sheets

APPARATUS FOR FORMING LONGITUDINAL THERMAL-FATIGUE CRACKS

CROSS REFERENCE

This application claims foreign priority under Paris Convention and 35 U.S.C. §119 to Korean Patent Application No. 10-2008-0107558, filed Oct. 31, 2008 with the Korean Intellectual Property Office.

BACKGROUND OF THE INVENTION

1. Field of the Invention

The present invention relates, in general, to an apparatus for forming longitudinal thermal-fatigue cracks on a tubular test piece in order to verify a technique of non-destructive inspection, and more particularly, to an apparatus for forming longitudinal thermal-fatigue cracks, in which, unlike a prior art in which circumferential cracks are formed by maximizing z-axial (longitudinal) stress selected from x-, y- and z-axial stresses, the longitudinal thermal-fatigue cracks are generated by maximizing y-axial (circumferential) stress selected from x-, y- and z-axial stresses generated by mounting on a tubular test piece a cooling block adapted to allow cooling water to flow in an inner space thereof in order to control a direction (longitudinal or circumferential direction) in which cracks occur, thereby ensuring effectiveness in terms of verification of a technique of non-destructive inspection.

2. Description of the Related Art

As well known in the art, safety-grade equipment of a nuclear power plant that is in operation is inspected according to an inspection period using non-destructive inspections which take into consideration the material, shape, predicted defects, etc. of the equipment in order to secure soundness of the equipment and stability of the plant.

Since such inspection of the nuclear power plant that is in operation is restrictive on accessibility, and provides important results relevant to lifespan prediction and safety evaluation of the equipment, a case is made to apply the non-destructive inspection which has actually proven defect detectability and is of high reliability.

In particular, the defect detectability of ultrasonic testing (UT) and eddy current testing (ECT) has been demonstrated using simulated test pieces based on machining methods in use up to the present. However, many cases that cause misgivings about the accuracy of defect detectability have occurred.

The non-destructive demonstration test pieces requested by a technology level applied to the nuclear power plant (ASME Section XI, Appendix VII) must include geometrical defects, implants, weld solidification cracks, lack of fusion, mechanical fatigue cracks, electrical discharging machine (EDM) notches and holes, thermal fatigue cracks, intergranular corrosion cracks (IGCC), and so on.

Among them, the thermal fatigue cracks are formed on the test piece using the following four methods.

First, the test piece is mounted on an autoclave, and is repetitively heated to high or low temperature under proper tensile or compressive stress.

Second, the tensile and compressive stresses are repetitively applied to the test piece at constant temperature.

Third, the temperature is repetitively varied without applying a mechanical load to the test piece.

Fourth, the test piece is constrained at opposite ends thereof, and is maintained at a constant temperature which is obtained using a conductive member or a high-frequency induction heater near the conductive member. Then, the test piece is subjected to thermal stratification by contacting it with cooling water.

However, the thermal fatigue cracks of the test pieces made using the first, second and third methods of forming the thermal fatigue cracks on the test piece differ from those generated from the equipment of the nuclear power plant or the process industry that is being actually operated in many aspects, so that the effectiveness of the verification of the technique of the non-destructive inspection cannot be positively ensured.

Further, in the fourth case, the test piece can be made so as to form the cracks similar to those generated from the equipment of the actual nuclear power plant, but it cannot positively guarantee the control of directions where the cracks are formed.

In order to overcome this problem, the applicant is granted an improved apparatus for forming thermal fatigue cracks as disclosed in Korean Patent No. 10-0801 404.

The apparatus for forming thermal fatigue cracks, which the applicant has previously filed for and been granted, is composed of a heating unit having a conductive member attached to an outer circumference of one side of a tubular test piece and an induction heating coil disposed adjacent to the conductive member, a cooling unit having a cooling water pump forcibly injecting cooling water from a cooling water reservoir to an inner circumference of the tubular test piece using a cooling water hose, and a control unit controlling the heating unit and the cooling unit. With this configuration, the reliability of the verification of the technique of the non-destructive inspection can be increased by forming the thermal fatigue cracks having characteristics similar to the thermal fatigue cracks generated from the equipment of the nuclear power plant or the process industry that is being actually operated.

However, the apparatus for forming the thermal fatigue cracks granted to the applicant can merely verify the technique of the non-destructive inspection in terms of the thermal fatigue cracks formed in a circumferential direction, so that an environment similar to that where natural cracks occur cannot be created, and thus the resulting effectiveness cannot help but be restrictively guaranteed.

In detail, the conventional apparatus for forming the thermal fatigue cracks cannot arbitrarily determine the direction where the cracks are formed, and thus non-destructive inspectors cannot acquire a technique capable of discriminating signals depending on the direction of the cracks in terms of the direction (longitudinal and circumferential directions) of the natural cracks generated from the equipment of the nuclear power plant or the process industry that is being actually operated.

SUMMARY OF THE INVENTION

Accordingly, the present invention has been made keeping in mind the above problems occurring in the related art, and embodiments of the present invention provide an apparatus for forming longitudinal thermal fatigue cracks, in which a cooling block is used for controlling thermal fatigue cracks similar to those generated from a nuclear power plant or a process industry which is actually in operation so that they are formed in a longitudinal direction rather than in a circumferential direction, thereby ensuring effectiveness in terms of verification of the technique of non-destructive inspection of the thermal fatigue cracks formed in the longitudinal direction in addition to the thermal fatigue cracks formed in the circumferential direction.

According to one aspect of the present invention, there is provided an apparatus for forming longitudinal thermal fatigue cracks. The apparatus comprises: a heating unit having an induction coil disposed adjacent to an outer circumference of one side of a tubular test piece, on an inner surface of which a notch is formed; a cooling unit having a cooling water pump and a cooling water hose which forcibly injects cooling water from a cooling water storage source into an inner circumference of the tubular test piece; a control unit controlling operation of the heating and cooling units; and a cooling block partially enclosing the outer circumference of the tubular test piece so as to control the magnitude of y-axial stress, supplied with a cooling source of fluid or gas from an outside so as to repetitively cool the tubular test piece heated by the heating unit to adjust a temperature gradient, and having a longitudinal slit for controlling crack positions.

According to another aspect of the present invention, the cooling block may be a tubular member that is in close contact with the outer circumference of the tubular test piece, and include cooling water lines therein along which cooling water or gas is circulated and which are connected to a cooler controlled by a cooling temperature controller.

According to another aspect of the present invention, the tubular test piece may be mounted on flat blocks at opposite ends thereof, each of which is of a plate shape and has a through-hole in a center thereof. The flat blocks may be connected with tension bars, each of which includes one selected from a cylinder using hydraulic or pneumatic pressure as working pressure, an actuator having a rod contacted or expanded by a supply of power, and an elastic bar having a damping characteristic, and are coupled with cooling water hoses of the cooling unit outside of the flat blocks.

Additional advantages, objects, and features of the invention will be more apparent from the following detailed description based on the accompanying drawings. First, the terms and words used in the present specification and claims should not be construed as being restricted to ordinary and customary meanings or dictionary definitions, but be interpreted to comply with the technical spirit of the present invention based on the principle by which an inventor can define the concepts implicated by terms in order to best describe his or her invention.

According to embodiments of the present invention, the apparatus for forming longitudinal thermal fatigue cracks forms thermal fatigue cracks very similar to those generated in a nuclear power plant or a process industry which is actually in operation, so that it can ensure effectiveness in terms of verification of a non-destructive inspection technique.

Particularly, the apparatus can form cracks very similar to longitudinal thermal fatigue cracks (hereinafter, referred to as "longitudinal natural cracks") generated from a nuclear power plant or a process industry that is actually in operation can be formed using circumferential thermal stress (tensile or compressive stress), so that it can ensure higher effectiveness so as to be able to control the direction in which the cracks are generated, as compared to the prior art.

BRIEF DESCRIPTION OF THE DRAWINGS

The above and other objects, features and advantages of the present invention will be more clearly understood from the following detailed description when taken in conjunction with the accompanying drawings, in which.

DETAILED DESCRIPTION OF THE INVENTION

The above and other objects, features and advantages of the present invention will be more clearly understood from the following detailed description.

Reference will now be made in greater detail to an exemplary embodiment of the invention with reference to the accompanying drawings.

First, it should be noted that, wherever possible, the same reference numerals will be used throughout the drawings and the description to refer to the same or like parts. Further, the detailed descriptions of known functions and constructions which would unnecessarily obscure the subject matter of the present invention will be avoided hereinafter.

Figure 1:
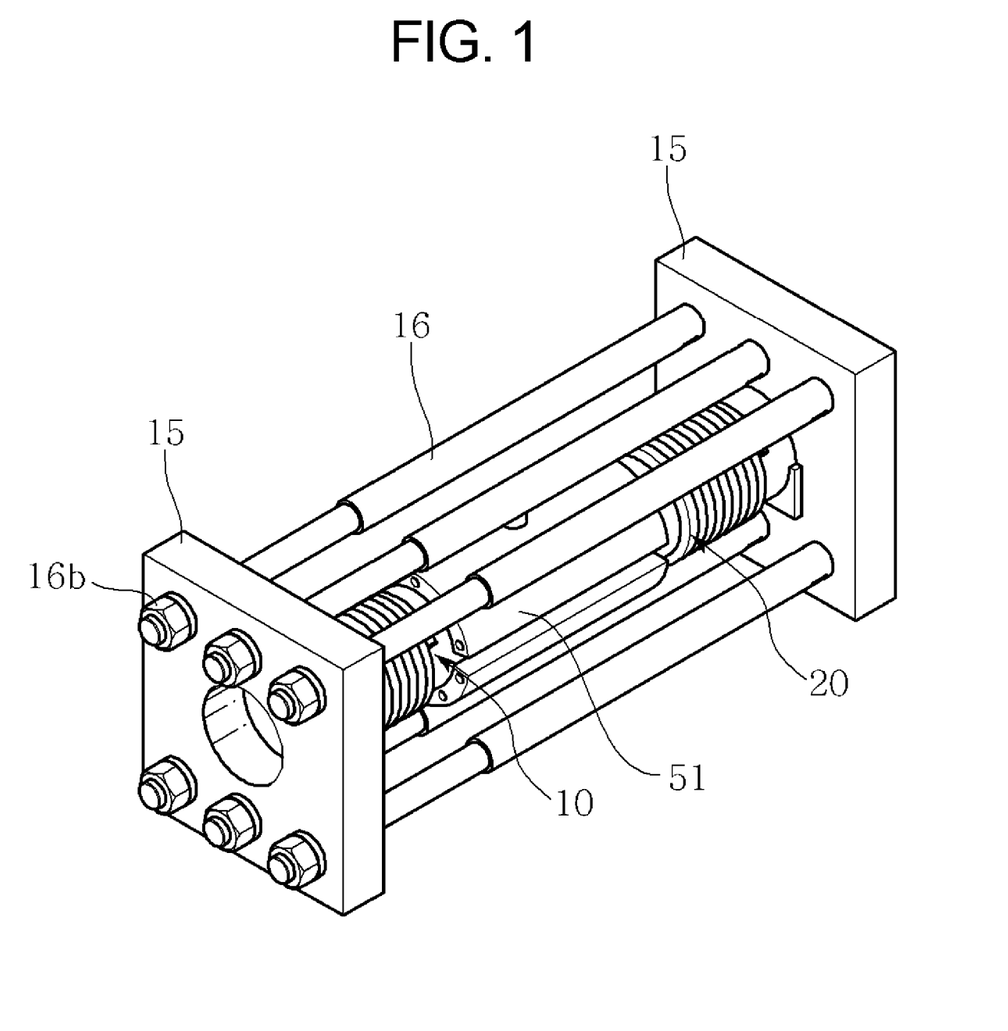
FIG. 1 is a partial perspective view illustrating a heating unit and a cooling block in an apparatus for forming longitudinal thermal fatigue cracks according to an exemplary embodiment of the present invention.
Figure 2:
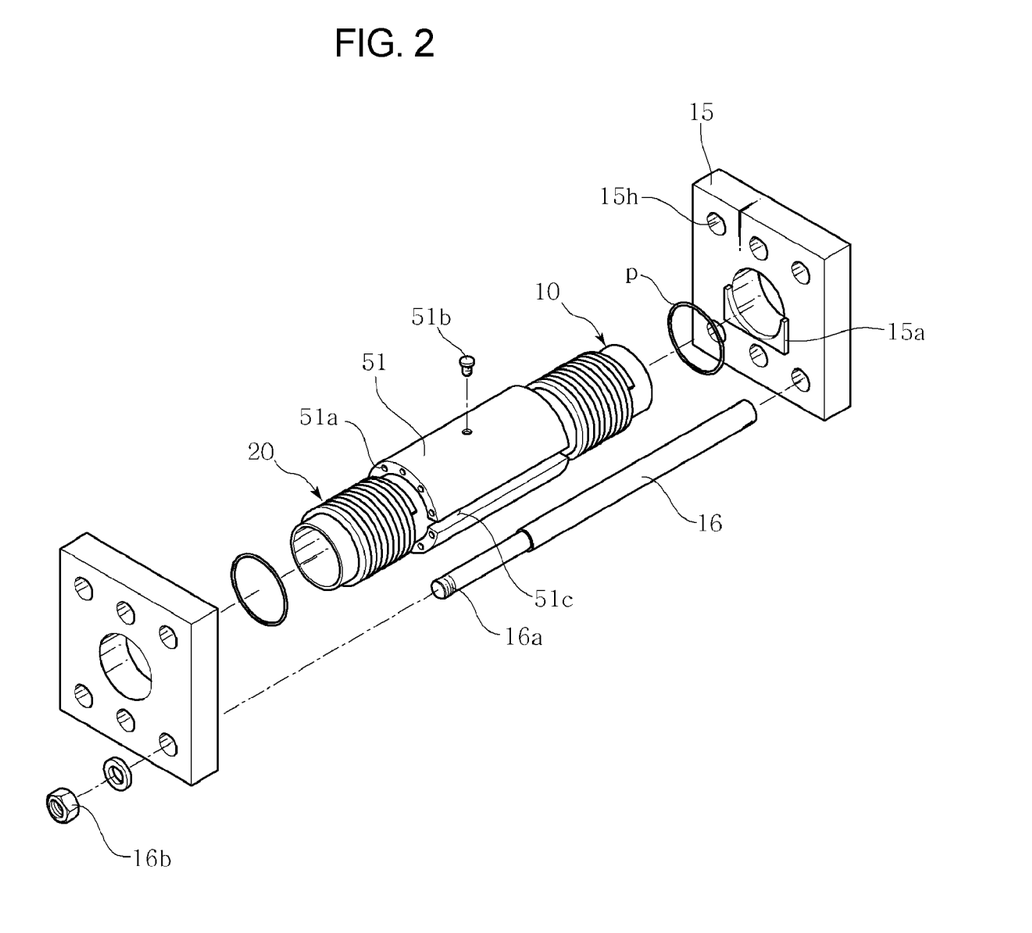
FIG. 2 is an exploded perspective view illustrating important parts in the apparatus for forming longitudinal thermal fatigue cracks illustrated in FIG. 1.

FIG. 1 is a partial perspective view illustrating a heating unit and a cooling block in an apparatus for forming longitudinal thermal fatigue cracks according to an exemplary embodiment of the present invention, and FIG. 2 is an exploded perspective view illustrating important parts in the apparatus for forming longitudinal thermal fatigue cracks illustrated in FIG. 1.

Figure 3:
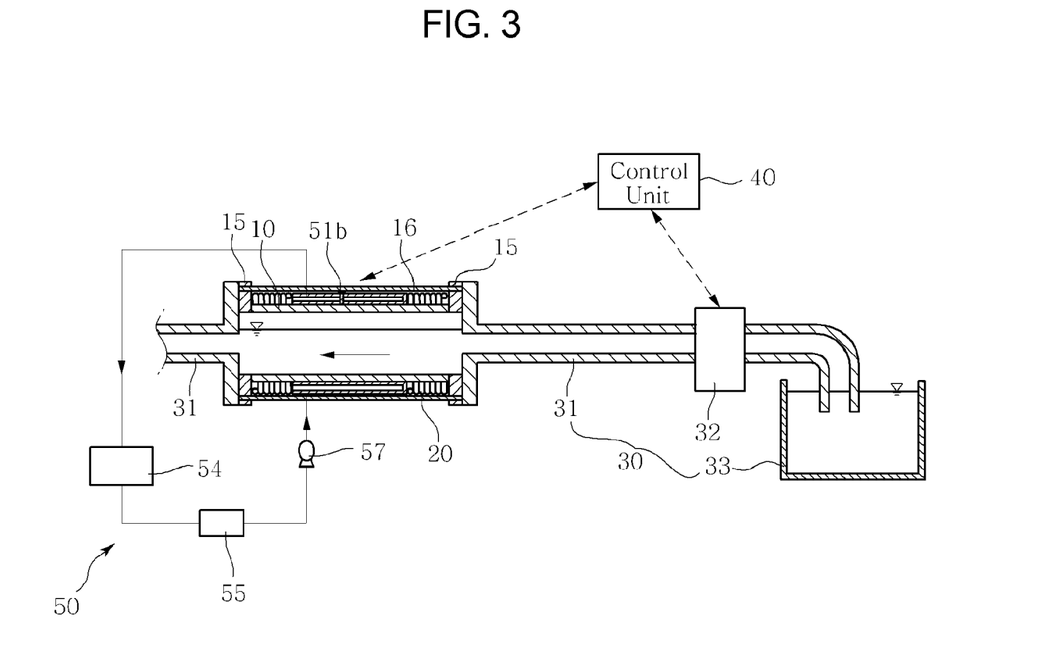
FIG. 3 conceptually illustrates the configuration of an apparatus for forming longitudinal thermal fatigue cracks according to an exemplary embodiment of the present invention.
Figure 4:
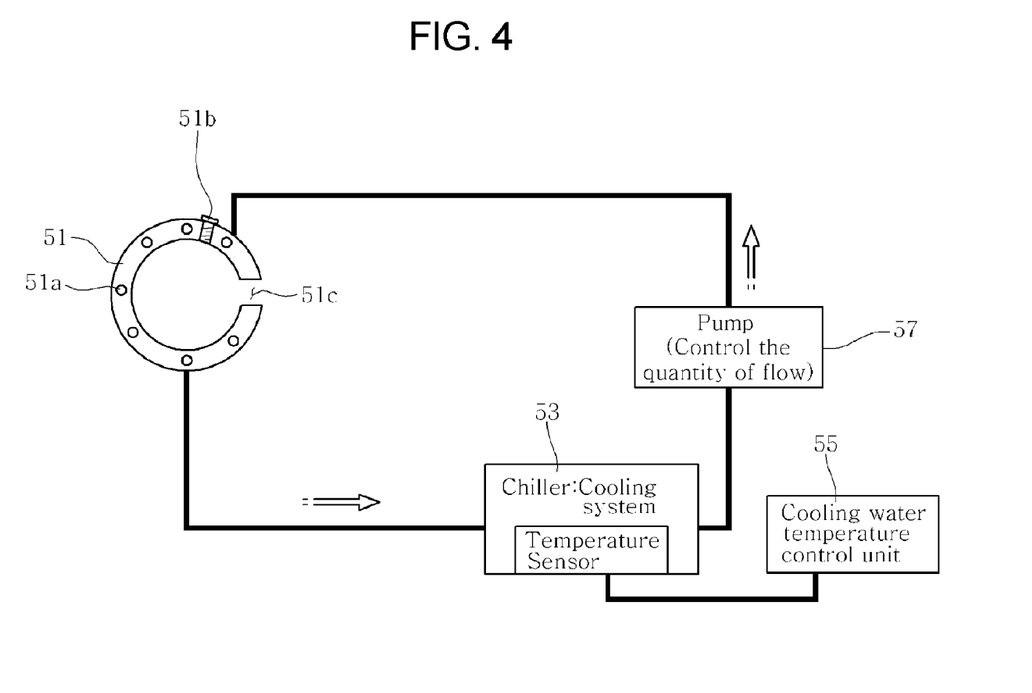
FIG. 4 is a schematic view explaining the configuration of a cooling block in an apparatus for forming longitudinal thermal fatigue cracks according to an exemplary embodiment of the present invention.

FIG. 3 conceptually illustrates the configuration of an apparatus for forming longitudinal thermal fatigue cracks according to an exemplary embodiment of the present invention, and FIG. 4 is a schematic view explaining the configuration of a cooling block in an apparatus for forming longitudinal thermal fatigue cracks according to an exemplary embodiment of the present invention.

As illustrated, according to an embodiment of the present invention, the apparatus 1 for forming longitudinal thermal fatigue cracks includes a heating unit 20 having an induction coil 22 disposed adjacent to an outer circumference of one side of a tubular test piece 10 on an inner surface of which a notch is formed, a cooling unit 30 having a cooling water pump 32 and cooling water hoses 31 which forcibly inject cooling water from a cooling water storage source into an inner circumference of the tubular test piece 10, and a control unit 40 controlling operation of the heating and cooling units 20 and 30.

Further, as illustrated in FIG. 2, a cooling block 51 includes cooling water lines 51a into which cooling water flows, a cooling water pump and a cooling water hose which inject the cooling water into the cooling water lines, and a temperature sensor and a temperature controller which control temperature of the cooling water.

The tubular test piece 10 can employ materials such as STS 304, STS 316, STS 321, STS 347, STS 308, STS 309, Inconel 600, Inconel 690, Inconel 800, Inconel X750, and Inconel 718, all of which are actually used in a nuclear power plant or a process industry.

This tubular test piece 10 includes at least one longitudinal notch of 100 mm or less formed on the inner circumference thereof through mechanical working such as lathe machining, chemical working caused by chemical corrosion, and so on. In the case in which numerous notches are formed on the inner circumference of the tubular test piece 10, crack formation time can be reduced as compared to the case in which no notch is formed.

Further, preferably, the tubular test piece 10 is not supported at opposite ends thereof such that circumferential (y-axial) stress has a maximum value in the state in which thermal stress is applied to the outer circumference of one side thereof by the heating unit 20.

In detail, the tubular test piece 10 is not supported at opposite ends thereof, making it easier to generate the circumferential (y-axial) stress using both flat blocks 15 having flanges 15a on which opposite ends of the tubular test piece 10 can be cradled, and packing rings p for watertight connection between the flat blocks 15 and the tubular test piece 10 can be installed in order to prevent water leakage as illustrated in FIG. 4.

The heating unit 20 includes the induction coil 22 that can directly heat the outer circumference of one side of the tubular test piece 10. Here, the induction coil 22 is connected with an external high-frequency current supply. When high-frequency current of the high-frequency current supply is applied to the induction coil 22, a high-frequency magnetic field is induced around the tubular test piece 10 enclosed by the induction coil 22. This high-frequency magnetic field causes the tubular test piece 10 to be heated by eddy-current loss or hysteresis loss. Thus, the outer circumference of one side of the tubular test piece 10 is heated to a predetermined temperature.

This heating unit 20 applies heat to the tubular test piece 10 so that it is heated to a predetermined temperature, so that it can generate thermal stress required to form the longitudinal thermal fatigue crack of the tubular test piece 10.

The cooling unit 30 is an element that forcibly injects cooling water into the inner circumference of the tubular test piece 10, thereby creating a cooling environment required to form the longitudinal thermal fatigue crack of the tubular test piece 10.

As illustrated in FIG. 3, this cooling unit 30 includes a cooling water storage tank 33 in which cooling water is stored, a cooling water pump 32 directly supplying the cooling water from the cooling water storage tank 33 to the inner circumference of the tubular test piece 10, and cooling water hoses 31 coupled with the flat blocks 15 outside the tubular test piece 10. One of the cooling water hoses 31 is connected to the cooling water storage tank 33 at one end thereof and the tubular test piece 10 at the other end thereof via the cooling water pump 32. Here, the cooling water hoses 31 can be sealed to the flat blocks 15 of the tubular test piece 10, for instance, by means of a packing.

Further, the flat blocks 15 are connected with tension bars 16, each of which includes one selected from a cylinder using hydraulic or pneumatic pressure as working pressure, an actuator having a rod contacted or expanded by supply of power, and an elastic bar having a damping characteristic.

According to an embodiment of the present invention, the cooling water is directly introduced into the inner circumference of the tubular test piece 10 by the cooling unit 30, so that the tubular test piece 10 forms a boundary similar to thermal stratification formed by a temperature difference between the inner circumference of the tubular test piece 10 and the fluid (i.e. the cooling water) flowing along the inner circumference of the tubular test piece 10, thereby generating circumferential thermal stress (tensile or compressive stress). Thus, cracks similar to longitudinal thermal fatigue cracks (hereinafter, referred to as "longitudinal natural cracks") generated from the nuclear power plant or process industry that is actually in operation can be formed using this circumferential thermal stress (tensile or compressive stress).

The control unit 40 is a control element that is electrically connected with the heating unit 20, the cooling unit 30 and the cooling block so as to control their operation, and thereby can apply control signals to them. This control unit 40 properly controls temperature of the cooling block, control conditions such as heating temperature, heating period, etc. of the heating unit 20, and control conditions such as an amount of cooling water, cooling period, etc. of the cooling unit 30. To this end, a computer such as a micro computer can be used.

Meanwhile, the configuration of the apparatus for forming longitudinal thermal fatigue cracks as described above is similar to that of the apparatus for forming thermal fatigue cracks, which has been previously filed for by the present applicant. However, according to an embodiment of the present invention, in order to be able to easily control positions where the longitudinal thermal fatigue cracks are generated in the tubular test piece 10, the cooling block 51 is fixedly mounted on the outer circumference of the tubular test piece 10. Thereby, the cooling block 51 cools the tubular test piece 10 heated by the heating unit 20. The heating and cooling of the tubular test piece 10 are repeated to adjust a temperature gradient. Thus, the positions where the longitudinal thermal fatigue cracks are generated from the tubular test piece 10 are controlled.

According to an embodiment of the present invention, the cooling block 51 maintains a predetermined portion of the tubular test piece 10 at a constant temperature (e.g. from 70° C. to 150° C.), thereby minimizing a longitudinal (z-axial) stress generated by repetition of the heating and cooling. Consequently, the cooling block 51 minimizes longitudinal bending of the tubular test piece 10. A shape and size of the cooling block 51 can be determined by the size of the tubular test piece 10. For example, as illustrated in the figures, the cooling block 51 has open opposite ends, and a longitudinal slit 51c for controlling crack positions.

Further, the cooling block 51 preferably has a diameter such that it is in close contact with the outer circumference of the tubular test piece 10. The cooling block 51 includes cooling water lines 51a therein along which cooling water or gas is circulated. The cooling water lines 51a are connected to a cooler 53 controlled by a cooling temperature controller 55.

This cooling block 51 is configured to be connected with the cooler 53 that is powered to generate a cooling source (cooling water (fluid) or cooling gas) so as to supply the cooling source. The cooler 53 is electrically connected with the cooling temperature controller 55, and thus is controlled by a control signal of the cooling temperature controller 55.

Meanwhile, the cooler 53 has a temperature sensor detecting temperature of the cooling source (cooling water or cooling gas). Information on the temperature detected by the temperature sensor is applied to the cooling temperature controller 55.

Among the reference numbers which have not been yet described, 51*b* indicates a screw member for fixing the cooling block 51 to the tubular test piece 10, and 57 indicates a pump for supplying the cooling source (cooling water or cooling gas) generated by the cooler 53 to the cooling block 51.

The heating unit 20, which is an element for adjusting the temperature gradient to the tubular test piece 10 along with the cooling block 51, is adapted to heat the tubular test piece 10 in part or in whole.

Figure 5:
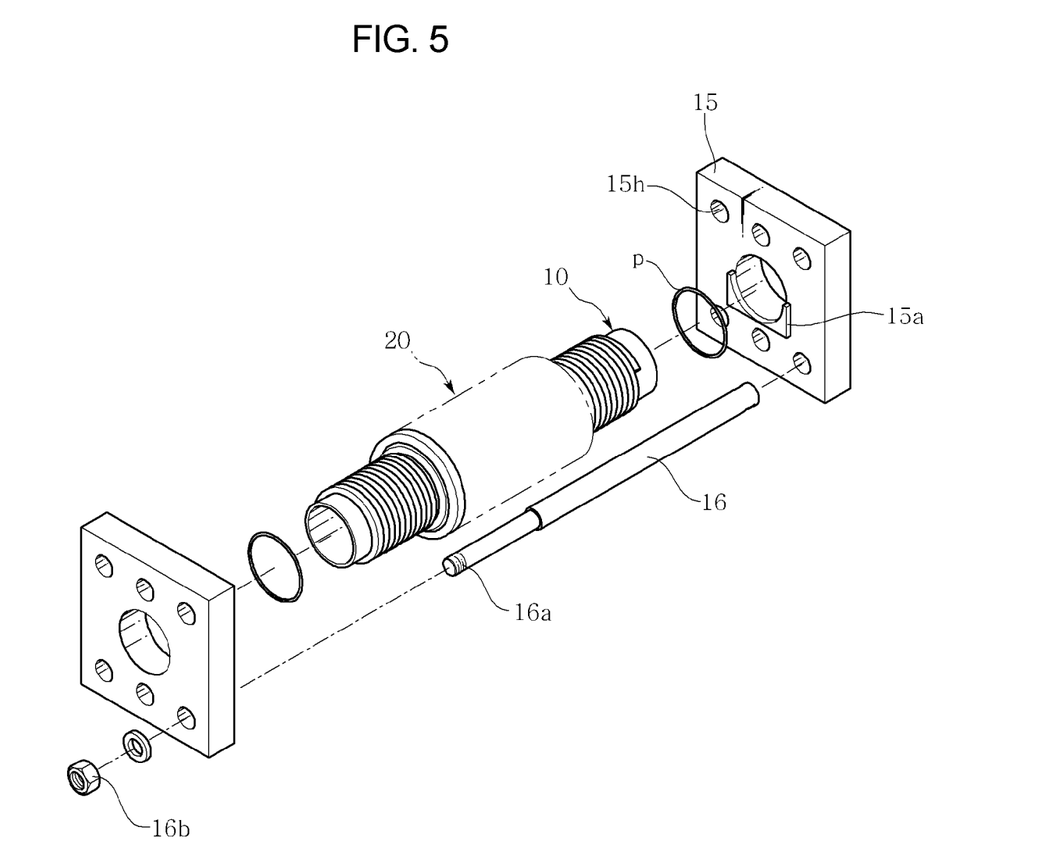
FIG. 5 is a perspective view illustrating another example where a heating unit is mounted in an apparatus for forming longitudinal thermal fatigue cracks according to an exemplary embodiment of the present invention.

In detail, the heating unit 20 is installed at a position where it does not interfere with the cooling block 51 installed on the tubular test piece 10, and thus locally heats the tubular test piece 10 as illustrated in FIG. 2. Otherwise, the heating unit 20 is wound around the entire tubular test piece 10 including the cooling block 51 so as to entirely heat the tubular test piece 10 as illustrated in FIG. 5.

The heating unit 20 configured in this way applies heat required to form the longitudinal thermal fatigue cracks of the tubular test piece 10.

The operation of the apparatus for forming longitudinal thermal fatigue cracks configured as described above will be described below with reference to FIG. 3.

As illustrated in FIG. 3, in the state in which the cooling block is mounted on the outer circumference of the tubular test piece 10, the high-frequency induction heat caused by the heating unit 20 is applied to part of the outer circumference of the tubular test piece 10 where the cracks are to be formed. Thereby, the part of the outer circumference of the tubular test piece 10 is subjected to high-frequency induction heating, and then the inner circumference of the tubular test piece 10 is cooled by the cooling unit. This process is repeated rendering possible the formation of longitudinal thermal fatigue cracks similar to naturally occurring cracks.

Experiments

The tubular test piece 10 used for this test employed STS 304 (O.D: 89 mm, t: 7.6 mm, and yield strength: 41.8 kg/mm$^2$) widely used as a structural member for a nuclear power plant.

This test piece had a length l of 500 mm, set an upper portion thereof where a crack was generated as zero degrees, and was given a chemical notch having a length of 30 mm in order to form a longitudinal natural crack in the proximity of 90 degrees.

At this time, the temperature of the cooling block 51 was continuously and for a long time maintained so as to be lower than room temperature (25° C.). In order to obtain the temperature gradient, the tubular test piece 10 was heated for 60 seconds using the heating unit 20, and was cooled for 30 seconds using the cooling block 51, so that a temperature difference ΔT of 350° C. was maintained at a position of 90 degrees of the tubular test piece 10.

Meanwhile, among the non-destructive inspection methods, ultrasonic testing was used to check whether or not the crack was generated. Whenever 3000 cycles were repeated it was checked whether or not the crack was generated. As a result, it was checked whether or not the cracks had grown at 6000 cycles, as illustrated in FIG. 6.

Figure 6:
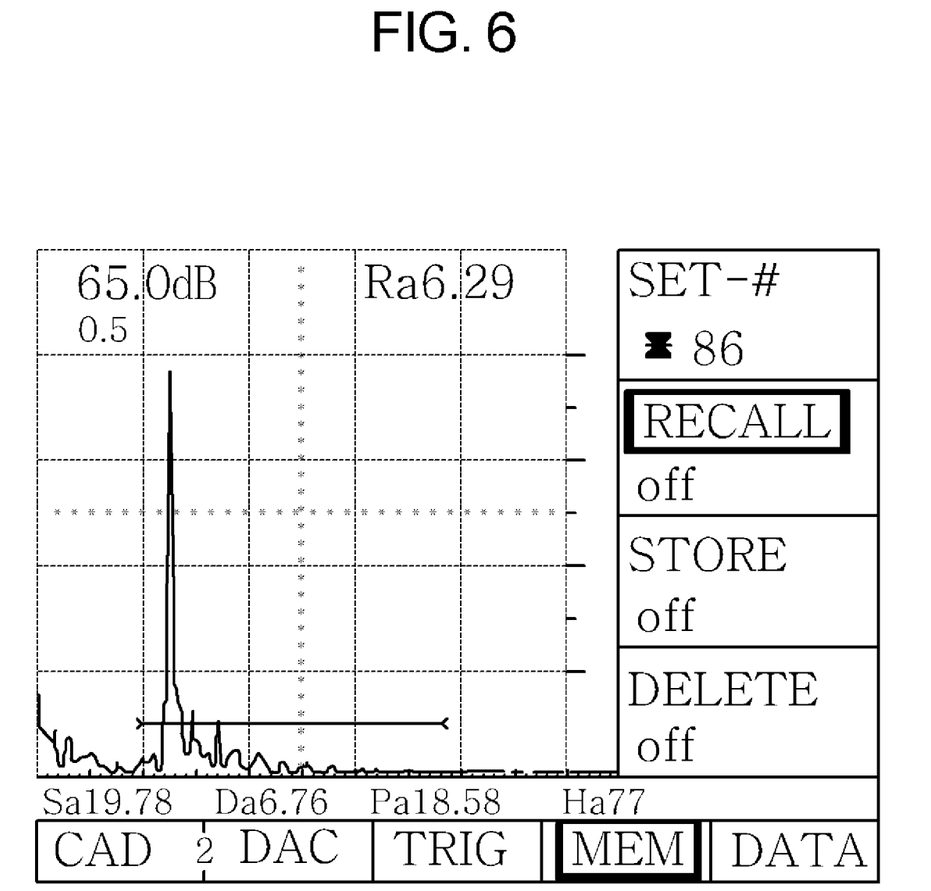
FIG. 6 is a photograph showing a signal generated by ultrasonic testing for checking whether or not a crack is generated by a tubular test piece.

After the test piece was cut, it was checked through liquid penetrant testing if the longitudinal natural crack was generated, as illustrated in FIG. 6.

Figure 7:
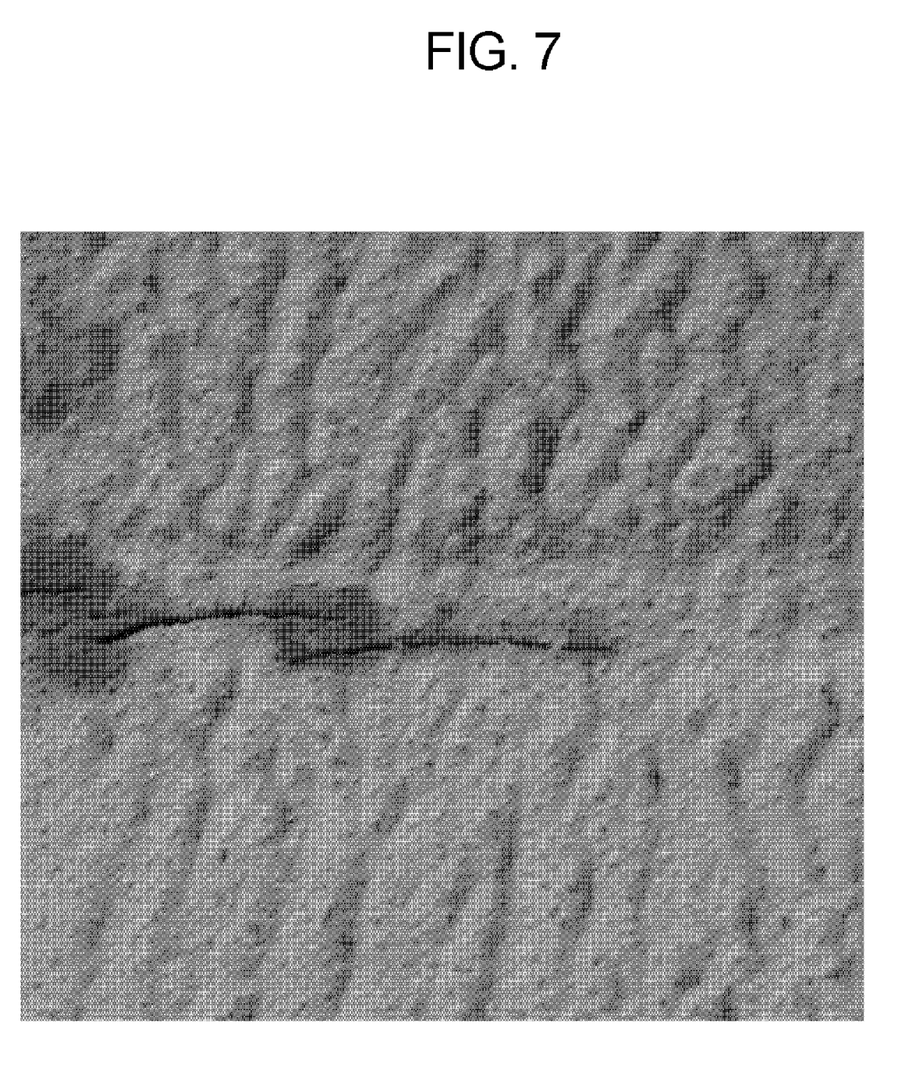
FIG. 7 is a photomicrograph taken on the basis of liquid penetrant testing for checking the direction of a crack generated by a tubular test piece.

Further, in the case of the test piece used in the apparatus for forming longitudinal thermal fatigue cracks according to an embodiment of the present invention, it could be checked from the photomicrograph of FIG. 7 that the longitudinal natural crack was generated, unlike the prior art.

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An apparatus for forming longitudinal thermal fatigue cracks, the apparatus comprising:
   a heating unit having an induction coil disposed adjacent to an outer circumference of one side of a tubular test piece, on an inner surface of which a notch is formed;
   a cooling unit having a cooling water pump and a cooling water hose which forcibly injects cooling water from a cooling water storage source into an inner circumference of the tubular test piece;
   a control unit controlling operation of the heating and cooling units; and
   a cooling block partially enclosing the outer circumference of the tubular test piece so as to control a magnitude of y-axial stress, supplied with a cooling source of fluid or gas from an outside so as to repetitively cool the tubular test piece heated by the heating unit to adjust a temperature gradient, and having a longitudinal slit for controlling crack positions.

2. The apparatus as set forth in claim 1, wherein the cooling block is a tubular member that is in close contact with the outer circumference of the tubular test piece, and includes cooling water lines therein along which cooling water or gas is circulated and which are connected to a cooler controlled by a cooling temperature controller.

3. The apparatus as set forth in claim 1, wherein the tubular test piece is mounted on flat blocks at opposite ends thereof, each of which has a plate shape and a through-hole in a center thereof, and wherein the flat blocks are connected with tension bars, each of which includes one selected from a cylinder using hydraulic or pneumatic pressure as working pressure, an actuator having a rod contacted or expanded by a supply of power, and an elastic bar having a damping characteristic, and are coupled with cooling water hoses of the cooling unit outside the flat blocks.

\* \* \* \* \*